(12) United States Patent
Joe et al.

(10) Patent No.: US 10,836,995 B2
(45) Date of Patent: Nov. 17, 2020

(54) SERUM-FREE MEDIUM ADDITIVE COMPOSITION CONTAINING PEROXIDASIN, AND USE THEREOF

(71) Applicant: THE CATHOLIC UNIVERSITY OF KOREA INDUSTRY-ACADEMIC COOPERATION FOUNDATION, Seoul (KR)

(72) Inventors: Young Ae Joe, Seoul (KR); Hyun-Kyung Kim, Yongin-si (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 80 days.

(21) Appl. No.: 15/781,207

(22) PCT Filed: Jan. 12, 2017

(86) PCT No.: PCT/KR2017/000414
§ 371 (c)(1),
(2) Date: Jun. 4, 2018

(87) PCT Pub. No.: WO2017/123021
PCT Pub. Date: Jul. 20, 2017

(65) Prior Publication Data
US 2018/0355307 A1    Dec. 13, 2018

(30) Foreign Application Priority Data

Jan. 15, 2016 (KR) .................. 10-2016-0005371
Jan. 11, 2017 (KR) .................. 10-2017-0004376

(51) Int. Cl.
*C12N 5/00* (2006.01)
*C12N 5/0735* (2010.01)

(52) U.S. Cl.
CPC .......... *C12N 5/0037* (2013.01); *C12N 5/0606* (2013.01); *C12N 2500/30* (2013.01); *C12N 2500/99* (2013.01); *C12N 2501/115* (2013.01); *C12N 2501/71* (2013.01)

(58) Field of Classification Search
CPC ............. C12N 5/0037; C12N 2501/71; C12N 2500/99; C12N 2500/30; C12N 2501/115; C12N 2501/998; C12N 2501/10; C12N 5/0031
See application file for complete search history.

(56) References Cited

U.S. PATENT DOCUMENTS

2012/0207705 A1* 8/2012 Kara .................. A61K 38/1709
                                                        424/85.2
2014/0171488 A1    6/2014 Joe et al.

FOREIGN PATENT DOCUMENTS

| KR | 10-0885854  | 2/2009  |
| KR | 10-1227047  | 1/2013  |
| KR | 10-1341316  | 12/2013 |
| WO | 2000-012526 | 3/2000  |

OTHER PUBLICATIONS

Nelson et al., Peroxidasin: a novel enzyme-matrix protein of *Drospohila* development. The EMBO Journal, vol. 13, No. 15 (1994) pp. 3438-3447. (Year: 1994).*
Mannello et al., Concise Review: No breakthrough for human mesenchymal and embryonic stem cell culture . . . . All that glitters is not gold! Stem Cells, vol. 25 (2007) pp. 1603-1609. (Year: 2007).*
Seung Woo Lee et al., "Peroxidasin is required for proper extracellular assembly of Col IV and FN in endothelial cells", 2014 KSBMB Annual Meeting, May 14, 2014.
Aida, Y. and M. J. Pabst, "Removal of endotoxin from protein solutions by phase separation using Triton X-114." J Immunol Methods vol. 132(2): 191-195, 1990.
Gautam Bhave et al., "Peroxidasin forms sulfilimine chemical bonds using hypohalous acids in tissue genesis" Nat Chem Biol 8(9): 784-790, 2012.
Guangjie Cheng et al., "Vascular peroxidase-1 is rapidly secreted, circulates in plasma, and supports dityrosine cross-linking reactions", Free Radic Biol Med 51(7): 1445-1453, 2011.
Guangjie Cheng et al., "Identification and characterization of VPO1, a new animal heme-containing peroxidase" Free Radic Biol Med 45(12): 1682-1694, 2008.
Michael J. Davies et al.,"Mammalian heme peroxidases: from molecular mechanisms to health implications." Antioxid Redox Signal, 10(7): 1199-1234, 2008.
Aaron L. Fidler et al., "A unique covalent bond in basement membrane is a primordial innovation for tissue evolution." Proc Natl Acad Sci of U.S.A., 111(1): 331-336, Jan. 2014.
Gordon, M. K. and R. A. Hahn, "Collagens." Cell Tissue Res 339(1): 247-257, 2010.
Jennifer R. Gotenstein et al., "The C. elegans peroxidasin PXN-2 is essential for embryonic morphogenesis and inhibits adult axon regeneration." Development 137(21): 3603-3613, 2010.
Hynes, R. O., "The extracellular matrix: not just pretty fibrils" Science 326(5957): 1216-1219, Nov. 2009.

(Continued)

*Primary Examiner* — Kara D Johnson
(74) *Attorney, Agent, or Firm* — Lex IP Meister, PLLC

(57) ABSTRACT

The present invention is related to a medium additive composition comprising peroxidasin for serum-free cell culture, and a method of performing serum-free culture of cells by using the same.

8 Claims, 12 Drawing Sheets

Specification includes a Sequence Listing.

(56) References Cited

OTHER PUBLICATIONS

Eric A. Jaffe et al., "Culture of human endothelial cells derived from umbilical veins. Identification by morphologic and immunologic criteria." J of Clinical Investigation, 52(11): 2745-2756, 1973.

Jamshid Khoshnoodi et al., "Mammalian collagen IV" Microsc Res Tech 71(5): 357-370, May 2008.

Lazar, E. et al., "Structure-function analysis of peroxidasin provides insight into the mechanism of collagen IV crosslinking." Free Radic Biol Med 83: 273-282, 2015.

Mouw, J. K., G. Ou and V. M. Weaver, "Extracellular matrix assembly: a multiscale deconstruction." Nat Rev Mol Cell Biol 15(12): 771-785, Dec. 1994.

Nelson, R. E. et al., "Peroxidasin: a novel enzyme-matrix protein of *Drosophila* development." EMBO J 13(15): 3438-3447, 1994.

Peterfi, Z. et al., "Peroxidasin is secreted and incorporated into the extracellular matrix of myofibroblasts and fibrotic kidney." Am J Pathol 175(2): 725-735, Aug. 2009.

Peterfi, Z. and M. Geiszt, "Peroxidasins: novel players in tissue genesis." Trends Biochem Sci 39(7): 305-307, 2014.

Rozario, T. and D. W. DeSimone, "The extracellular matrix in development and morphogenesis: a dynamic view." Dev Biol 341(1): 126-140, 2010.

Errol S. Wijelath et al., "Heparin-II domain of fibronectin is a vascular endothelial growth factor-binding domain: enhancement of VEGF biological activity by a singular growth factor/matrix protein synergism." Circ Res 99(8): 853-860, 2006.

\* cited by examiner

[Fig. 1]
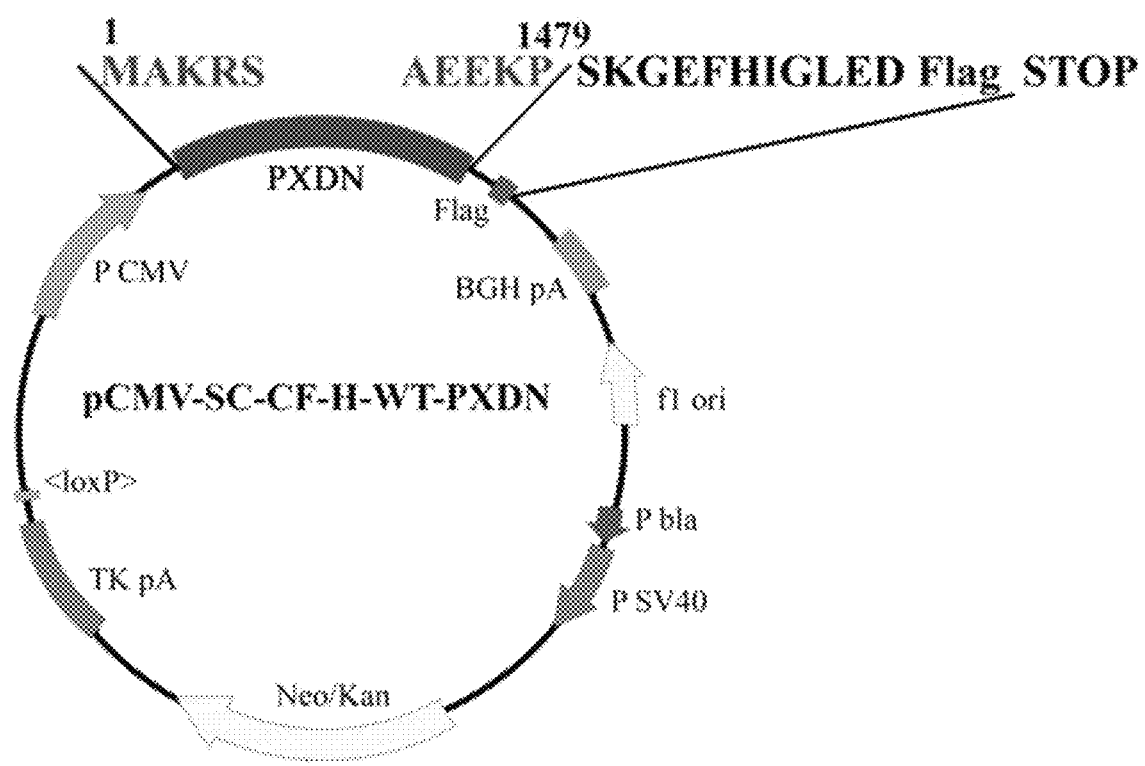

[Fig. 2a]
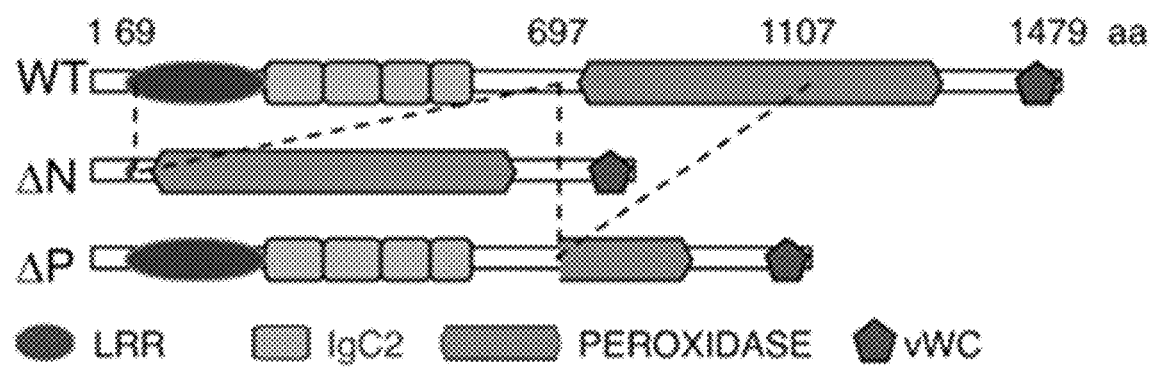
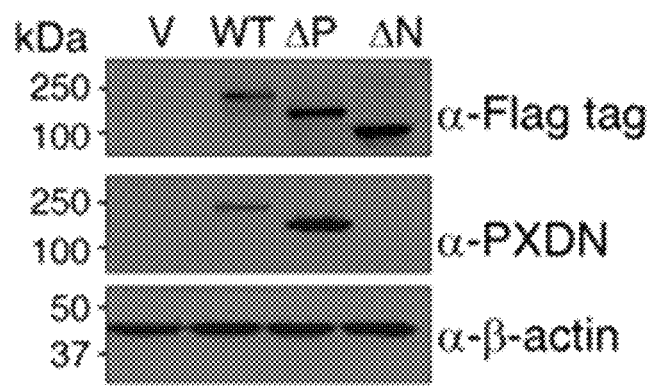

[Fig. 2b]
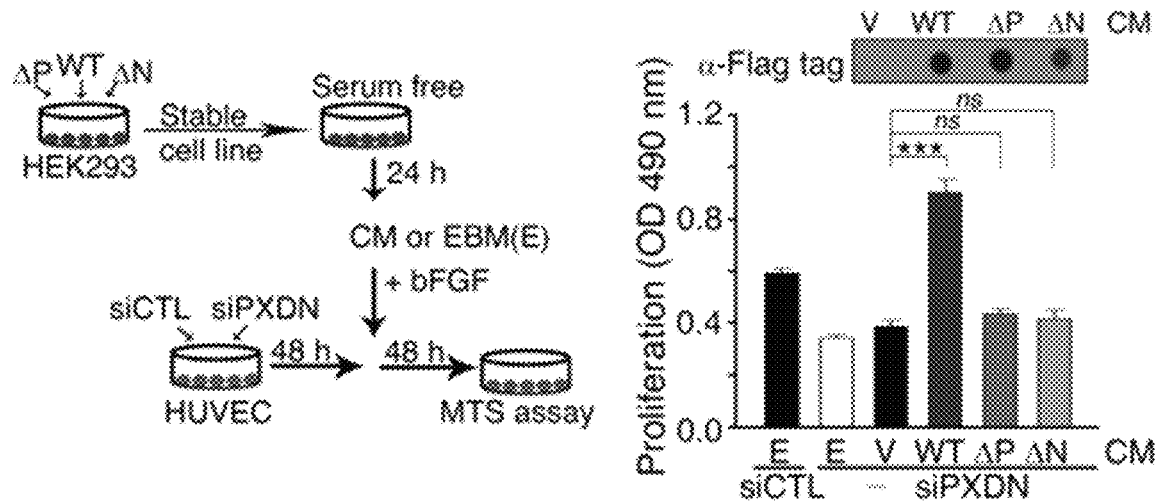
[Fig. 2c]
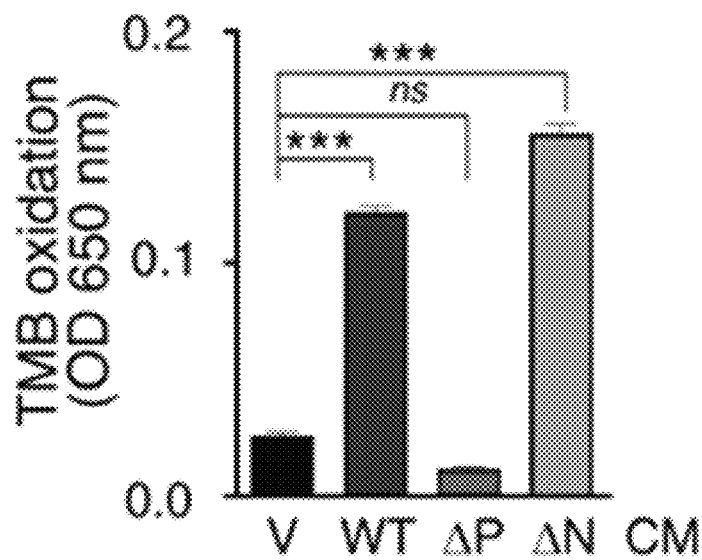

[Fig. 3a]
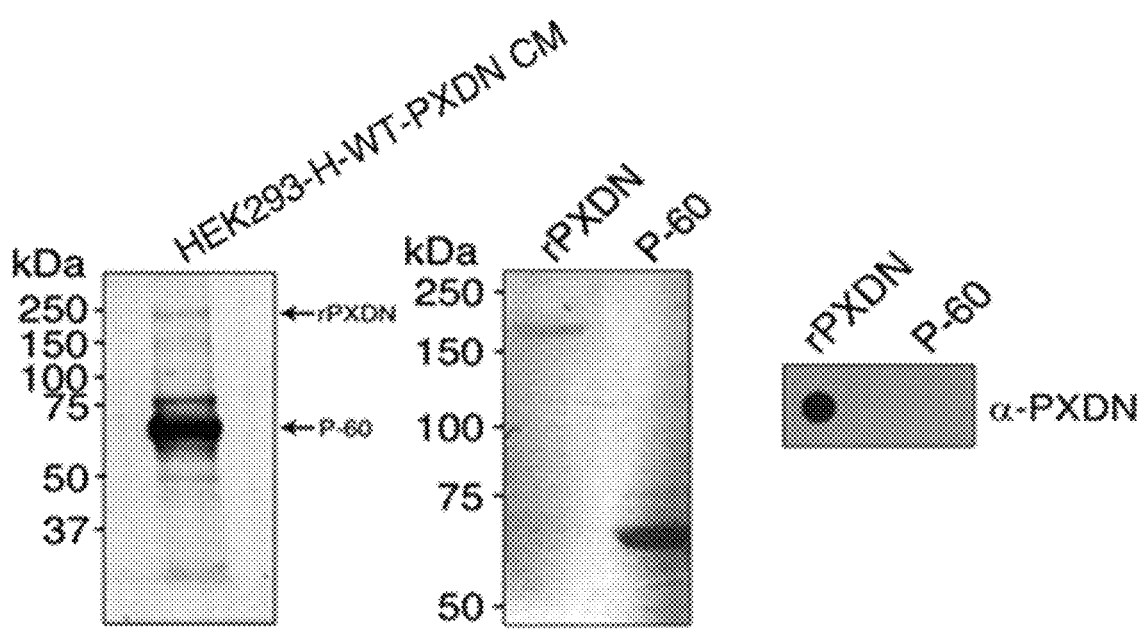
[Fig. 3b]

[Fig. 3c]
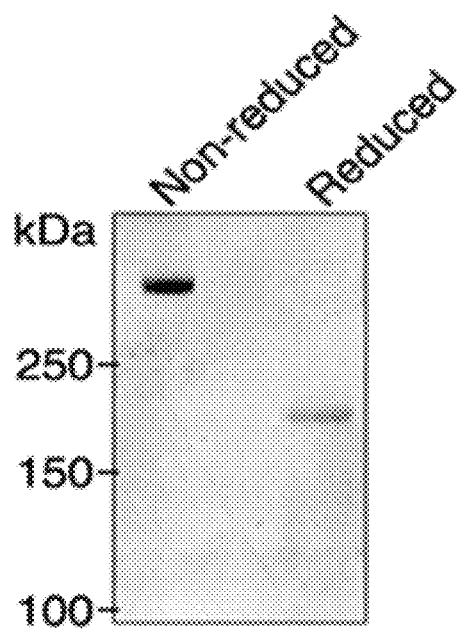
[Fig. 3d]
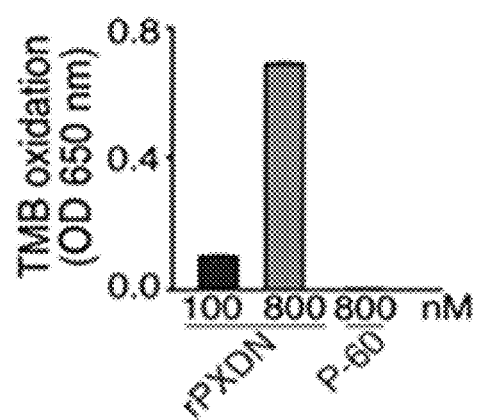

[Fig. 4a]
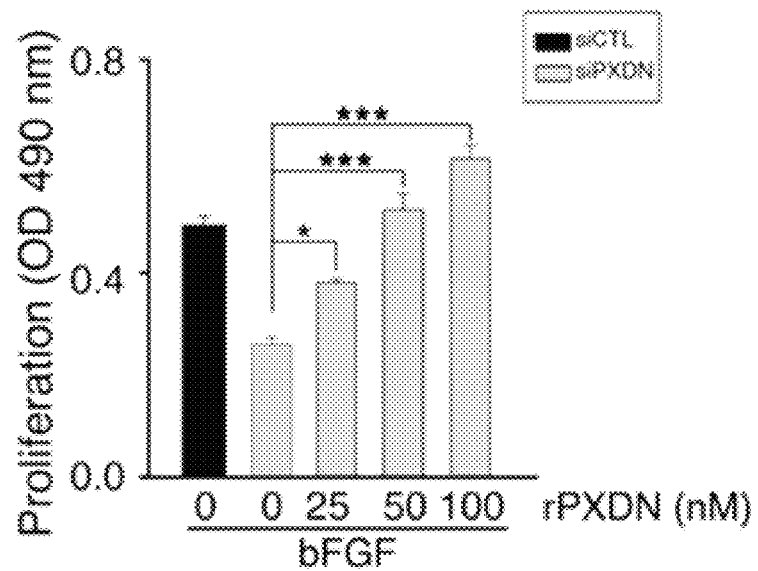
[Fig. 4b]
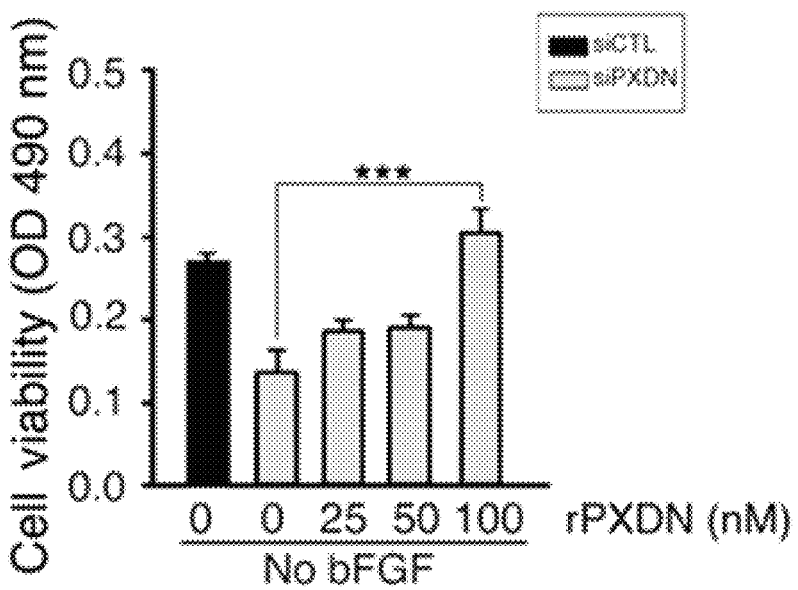

[Fig. 5a]
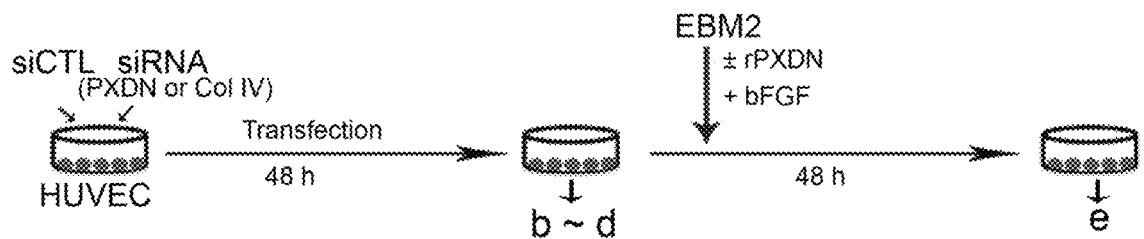
[Fig. 5b]
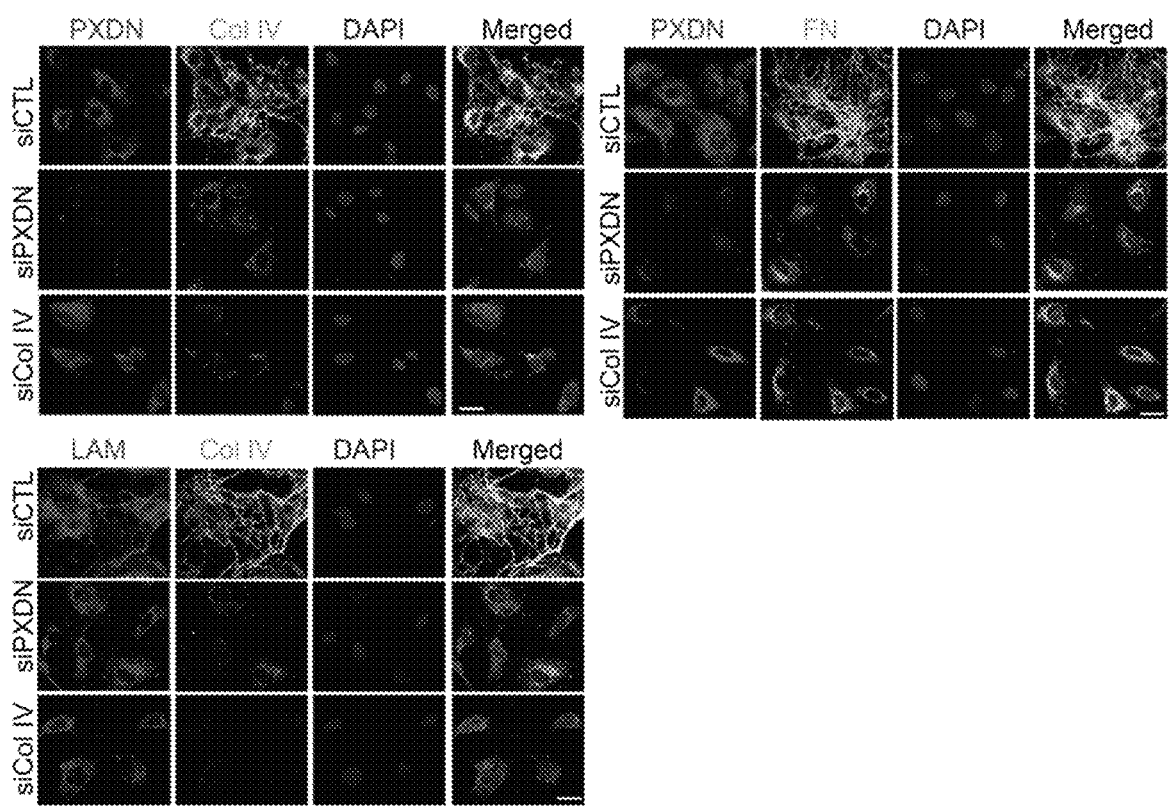

[Fig. 5c]
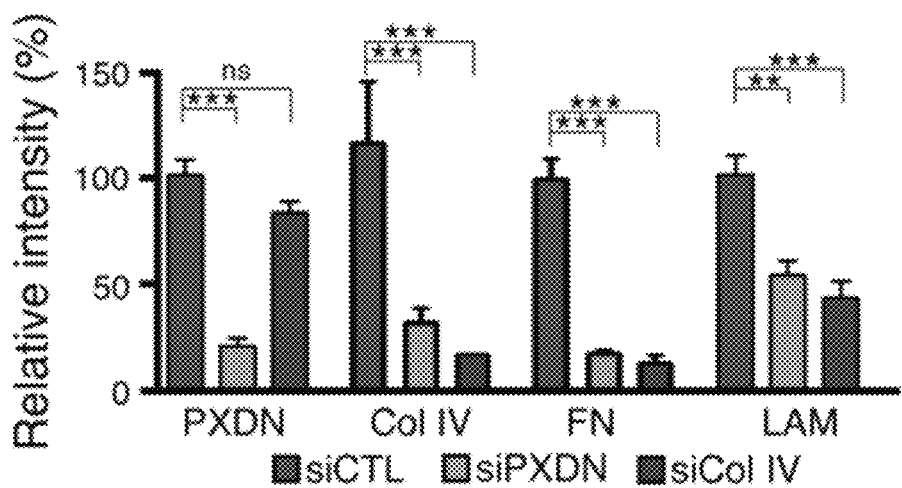
[Fig. 5d]
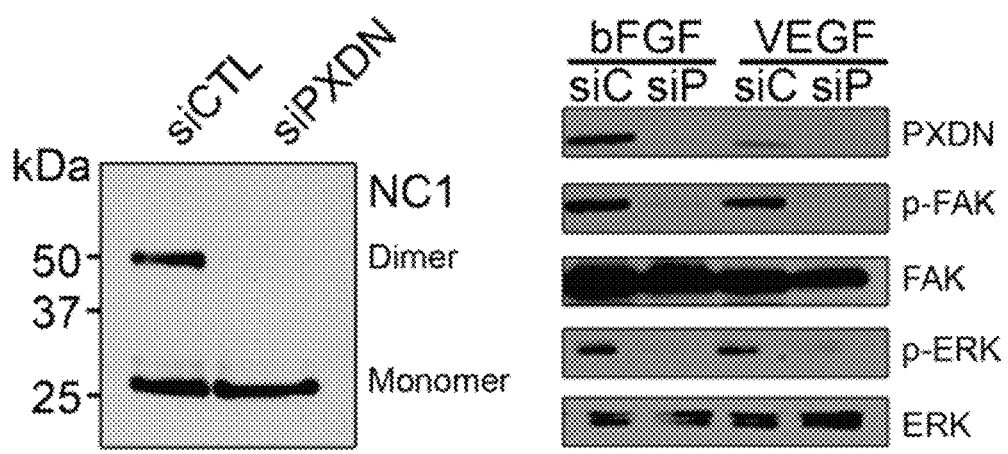

[Fig. 5e]
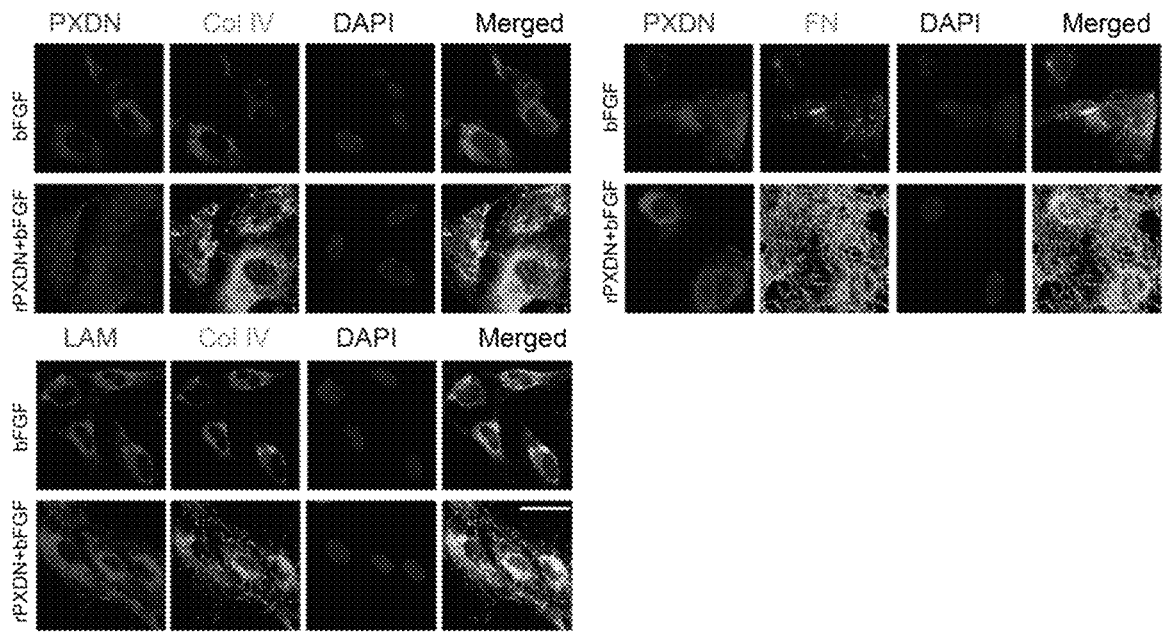
[Fig. 6a]
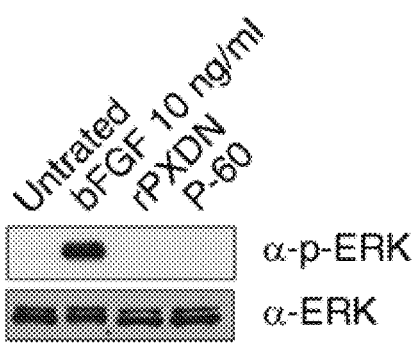

[Fig. 6b]
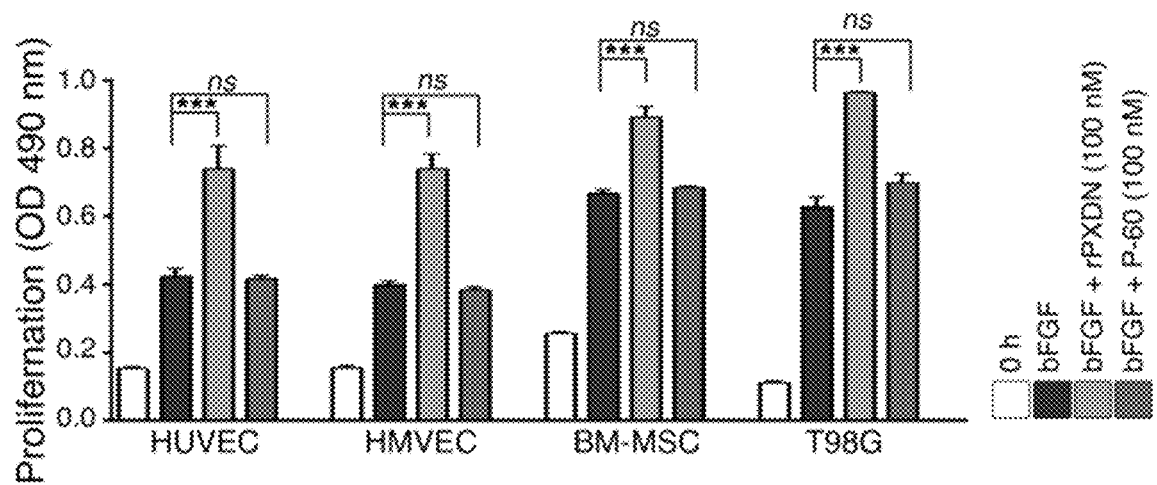
[Fig. 6c]
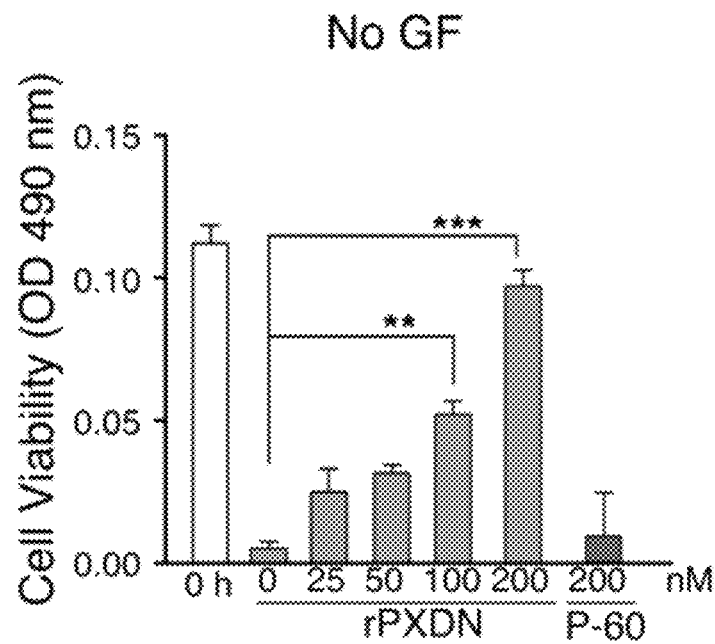

[Fig. 6d]
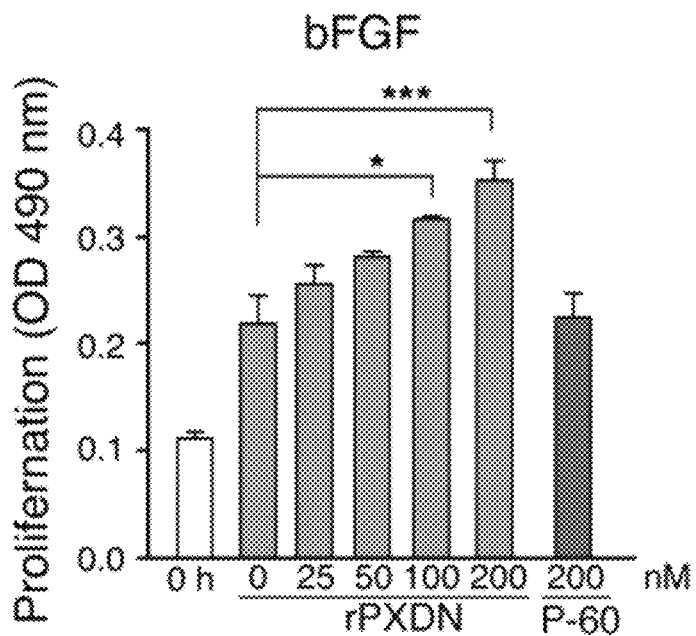
[Fig. 6e]
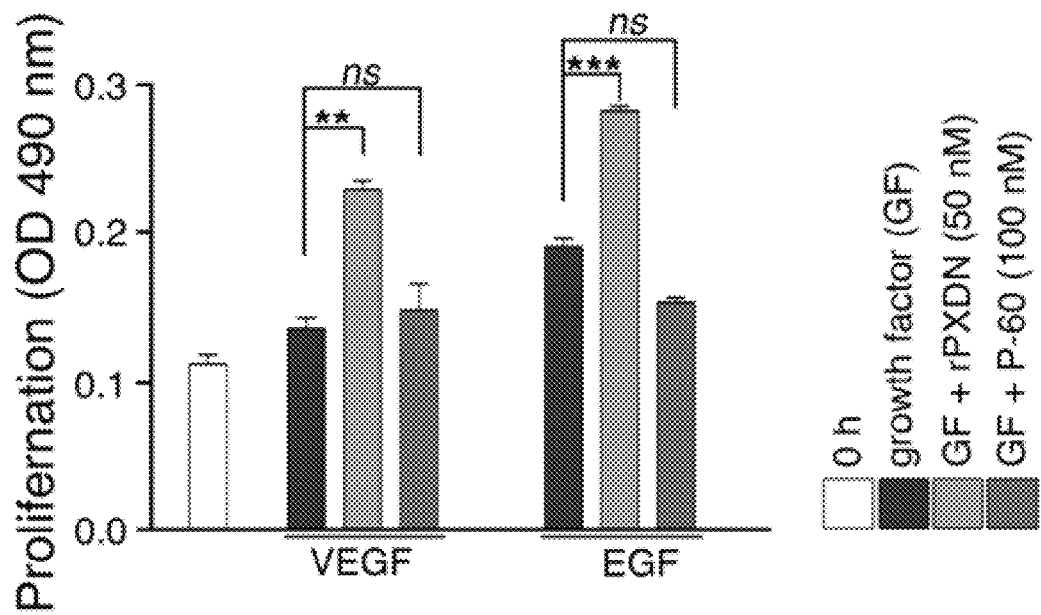

[Fig. 7a]
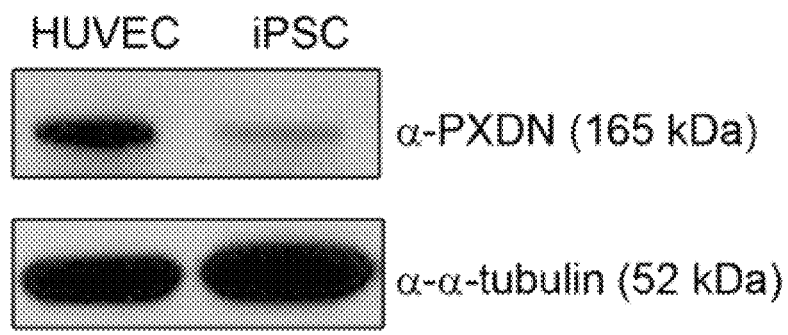
[Fig. 7b]
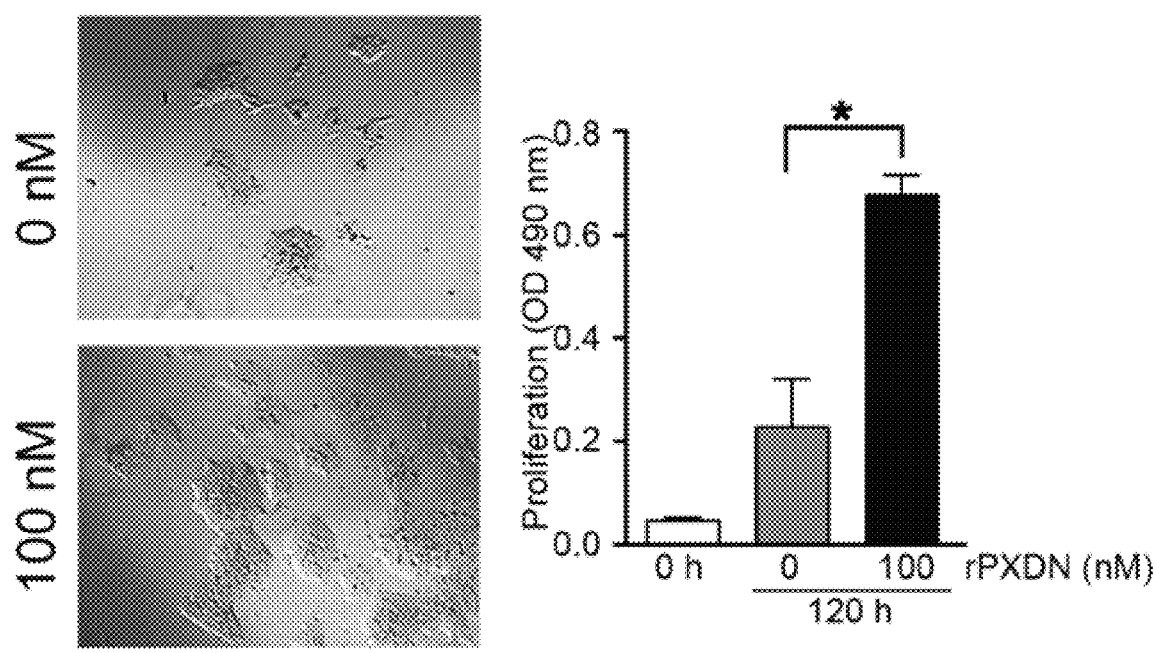

SERUM-FREE MEDIUM ADDITIVE COMPOSITION CONTAINING PEROXIDASIN, AND USE THEREOF

TECHNICAL FIELD OF THE INVENTION

The present invention relates to a medium additive composition for serum-free cell culture, comprising peroxidasin, and a method for serum-free cell culture using the same.

BACKGROUND ART

Stem cells are cells having pluripotency that can differentiate into cells from endoderm, mesoderm and ectoderm of an animal, or multipotency that can differentiate into cells closely related in tissue or function. Stem cells include embryonic stem cells, adult stem cells and induced pluripotent stem cells, etc.

Stem cells have been applied variously in clinical trials, for example, human mesenchymal stem cells, one of adult stem cells, free from the general issues of embryonic stem cells like carcinogenesis or ethical issues, have been used as cell therapeutics for regeneration of injured tissue in cardiovascular, nervous, and musculoskeletal systems by in vitro culture, or for the purpose of reducing homologous immune response or facilitating hematopoietic cell transplantation.

Since the number of stem cells obtained from the tissue is very small, it is necessary to culture the stem cells stably in vitro and expand, for various clinical applications of stem cells.

In addition, hormones, enzymes, cytokines, or therapeutic antibodies used for medicines are mostly recombinant glycoproteins. Because the functional activity of the glycoproteins is lost when they are produced from prokaryotes, it is produced in complex eukaryotes like animal cells (e.g. CHO cell, BHK cell, NS0 cell, etc.). Therefore, the technique of stably culturing cell in vitro is also necessarily required in mass culture of animal cells for producing biopharmaceuticals such as recombinant proteins or gene therapeutics.

Conventionally, when culturing stem cells or animal cells in vitro, culturing medium including non-human animal-derived serum such as fatal bovine serum have been used. Serum is added to medium as a source of nutrients promoting cell growth or proliferation, or a source of biological activity substances such as hormones. However, serum brings the increase of medium price due to its high-price, and difficulties in protein purifications because of the components complexity, as well as different results in experiments because components are different in each production process. In addition, the safety problems of animal serum have been pointed out because it has relatively high risks of infection by various pathogens such as microorganisms, viruses, or prions and may arise of inappropriate immune responses.

Therefore, the technique to culture cells without non-human animal-derived serum has been developed. For example, in the case of cell culture for autologous transplantation, contamination of cells could be avoided by using autologous human serum obtained from the same patient however there is a problem that a large amount of blood is required for the serum production. In addition, serum-free culture medium without serum or low-serum culture medium including less serum has been developed, however there are following problems: such a medium only allows specific cells to grow well; the cell growth factors replacing serum are too expensive; the cell growth and the product production are more unstable than serum-containing medium.

In addition, in case of the stem cells used as cell therapeutics, stem cells obtained from a patient are cultured in vitro, and re-injected to the patient. Since the safety of such a culturing process for human body must be guaranteed, discovery of the serum substitutes which can substitute animal serum is very meaningful commercially.

On the other hand, peroxidasin was first discovered in Drosophila, and it was suggested that peroxidasin plays an important role in matrix formation and consolidation in Drosophila hemocyte (Nelson, Fessler et al. 1994). The peroxidasin of Drosophila is composed of 1512 amino acid residues and is known to form trimer. A peroxidasin molecule of human is composed of 1479 amino acids and carries several ECM motifs containing leucin-rich repeats (LRR), immunoglobulin C2 (IgC2)-type domain and von Willebrand factor type C (vWC) and the peroxidase domain.

However, the function of peroxidasin promoting cell proliferation and survival in serum-free medium has not been known as yet.

DETAILED DESCRIPTION OF THE INVENTION

Technical Problem

The present invention provides a use of peroxidasin as a medium additive for not only alternative of animal serum, but also promoting cell proliferation and survival.

In one aspect, a medium additive composition for serum-free culture of cells comprising peroxidasin is provided.

In another aspect, a medium for serum-free culture of cells, comprising the medium additive composition described above is provided.

In the other aspect, a method of serum-free culture of cells comprising a step of culturing cells in the medium described above is provided.

Technical Solution

In one aspect to achieve the objects, the present invention relates to a medium additive composition for serum-free culture of cells, comprising peroxidasin.

In another aspect, the present invention relates to a medium for serum-free culture of cells comprising the medium additive composition described above.

In the other aspect, the present invention relates to a method of serum-free culture of cells comprising the step of culturing cells in the medium described above.

Hereinafter, the present invention will be described in more detail.

The term, "serum-free culture", as used herein, refers to cell culture that the medium does not contain completely or substantially serum derived from human or non-human animal.

The phrase, "substantially not containing serum derived from animal", as used herein, might refer to the inclusion of serum derived from animal at a lower level than the amount being conventionally added to the medium, or at an amount not doing affect substantially cell proliferation or survival. For example, it may refer to that the serum derived from animal is contained at 5% or less, 4% or less, 3% or less, 2% or less, 1% or less, 0.5% or less, or 0.1% or less in the medium.

In the present invention, there is no particular limitation on the basic medium for serum-free culture. For example, basic culture medium for animal cell well-known in the art can be used. In one embodiment, DMEM (Dulbecco's Modified Eagle's Medium), MEM (Minimal Essential Medium), IMDM (Iscove's Modified Dulbecco's Medium), α-MEM (alpha-minimum essential medium), M199 (Medium 199), RPMI (Roswell Park Memorial Institute) 1640, BME (Basal Medium Eagle), GMEM (Glasgow's Minimal essential Medium), EGM2 (endothelial growth medium 2)-MV, Ham's F-12, Ham's F-10, E199, MCDB, Leibovitz L-15, or Williams Medium E may be exemplified but not limited thereto. The basic medium can be used alone or in combination.

In the present invention, peroxidasin derived from any organisms can be used, as long as it has activity promoting proliferation or survival of cells in serum-free culture. Preferably human-derived peroxidasin can be used. The sequence information of peroxidasin is available through public databases. For example, a nucleotide sequence of human peroxidasin gene is available in Genbank Accession number NM_012293.1, and the amino acid sequence is available in Genbank Accession number NP_036425.1.

Even if some sequences of peroxidasin proteins are changed, it is included in the present invention as long as it maintains the activity of promoting cell proliferation or survival in serum-free culture. Compared to the reference protein without sequence changes, the sequence variants can include substitutions, deletions, additions and/or insertions of amino acids of the proteins which exhibit similar or equivalent biological activity to the reference protein, for example, wild type protein. In this regards, "sequence homology", as used herein, refers to similarity with amino acid sequence or nucleotide sequence of wild type or reference protein. The present invention may include proteins having equivalent biological activities to wild type protein, while the proteins have at least 60%, at least 65%, at least 70%, at least 75%, at least 80%, at least 85%, at least 90%, at least 95%, at least 98%, or at least 99% of the same amino acid sequence as the wild type peroxidasin protein. The homologous protein may include the same active domain with target proteins. This homology comparison can be performed with naked eyes or a comparison program being easily purchased. Computer programs in market can calculate homology among at least two (2) sequences as percentage (%), and the homology (%) can be calculated for adjacent sequences. Sequence alignment methods for comparison can be performed using methods known in the art and for example, include GAP, BESTFIT, BLAST, FASTA and TFASTA.

Amino acid substitutions in proteins and peptides that do not alter overall activity are known in the art. For example, substitutions generally occurred may be, but are not limited to, substitutions between amino acid residues of Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, or Asp/Gly.

Depending on the case, modification of peroxidasin proteins may be carried out such as phosphorylation, sulfation, acrylation, glycosylation, methylation or farnesylation to in the range of maintaining the overall molecular activities. In addition, the present invention may include protein variants whose structural stability against heat or pH, or activity is increased by the change or modifications of in amino acid sequence.

In the present invention, peroxidasin can be obtained by various methods. For example, it can be obtained by extraction and purification from nature in a manner well known in the art. Alternatively, it can be obtained as a synthetic protein chemically synthesized or a recombinant protein obtained by gene recombination technique. In case of the synthetic protein using the chemical synthesis, it can be obtained by polypeptide synthesis methods well known in the art. In case of gene recombination technique, peroxidasin can be obtained by the following steps: inserting peroxidasin protein coding nucleic acids to an appropriate expression vector, introducing the vector to host cells, culturing the host cells to express the target protein, and collecting the peroxidasin protein from the host cells. After the protein is expressed in the selected host cells, conventional biochemical separation techniques, for example, treatment with protein precipitants (salting out method), centrifuge, sonication, ultrafiltration, dialysis or various chromatography techniques such as molecular sieve chromatography (gel filtration), adsorption chromatography, ion exchange chromatography, affinity chromatography and the combination thereof may be used conventionally to separate proteins at a high purity. The gene encoding peroxidasin can be separated, synthesized by standard molecular biology techniques such as chemical synthesis method or recombination method, or obtained commercially.

In the present invention, the medium additive composition or medium composition may include a recombinant vector containing peroxidasin-coding gene, a cell transformed with the vector described above, a culture of the cell or a purified peroxidasin.

The recombinant vector can be operably linked to regulatory sequence of transcription and translation that can function for selected expression in host in order to increase the expression level of the inserted gene. The recombinant vector is a gene construct comprising essential regulatory elements operably linked to a gene insert, and the gene construct can be prepared by standard recombinant DNA technique. The kinds of the recombinant vector is not particularly limited, as long as it functions in expressing a target gene in various host cells such as prokaryotic cells and eukaryotic cells and producing target proteins. However, a vector being capable of producing foreign proteins similar to the natural form in a large amount, it preferably has high expression activity and includes a promoter showing strong activity. Preferably, the recombinant vector comprises at least a promoter, a start codon, a gene encoding the target protein, a stop codon and a terminator. In addition, the recombinant vector may include a DNA encoding signal peptide, an enhancer sequence, untranslated regions (UTR) of 5' and 3' end of the target gene, a selection marker region or a replicon.

A method of introducing the recombinant vector into a cell can be, but not limited to, a conventional methods known in the art, for example, calcium phosphate method, calcium chloride/rubidium chloride method, electroporation, electroinjection, heat shock, and chemical treatment method such as PEG, gene gun, retroviral infection, microinjection, DEAE-dextran, and cationic liposome.

A prokaryotic cell or a eukaryotic cell can be used as a cell to which a recombinant vector is introduced and a peroxidasin is expressed. A cell having a high efficiency of introducing DNA and a high expression efficiency of the introduced DNA can be used. To suitably perform cell growth and massive production of peroxidasin protein, cells expressing peroxidasin can be cultured under appropriately controlled conditions such as temperature, pH of medium and culturing time. In one embodiment, the expression of peroxidasin can be induced by using IPTG (isopropyl-b-D- thiogalactopyranoside) as an inducing factor in cell culture, and the induction time can be adjusted to maximize the amount of protein. The expressed peroxidasin can be separated and purified by the conventional biochemical separation techniques described above, after cell disruption.

In the present invention, the compositions of medium additive or the medium compositions may also include a culture of cells into which recombinant vector including peroxidasin is introduced. The culture can be a culture comprising peroxidasin-introduced cell or a conditioned medium from which cells are removed, and a culture that comprises peroxidasin secreted from cells.

In the present invention, the composition of the medium additive or the composition of medium may further comprise growth factors together with peroxidasin. The growth factors can be, but are not limited to, at least one selected from the group consisting of, for example, fibroblast growth factor (FGF), basic fibroblast growth factor (bFGF), vascular endothelial growth factor (VEGF), epidermal growth factor (EGF), connective tissue growth factor (CTGF), insulin-like growth factor (IGF), transforming growth factor (TGF), nerve growth factor (NGF), hepatocyte growth factor (HGF), platelet-derived growth factor (PDGF), bone-derived growth factor (BDGF), stem cell factor, leukemia inhibitory factor (LIF), Brain-derived neurotrophic factor (BDNF), glial-derived neurotrophic factor (GDNF), Activin A, Noggin, bone morphogenetic protein 2 (BMP2), bone morphogenetic protein 4 (BMP4), Angiopoietin-1, sonic hedgehog (SHH), Wnt, FLT-3 ligand (FMS-related tyrosine kinase 3 ligand), and colony stimulation factor (CSF).

Stem cells or progenitor cells can be exemplified as the cells which can be cultured in the medium of the present invention, but are not limited to. The stem cells include embryonic stem cells, adult stem cells and induced pluripotent stem cells.

Adult stem cells refer to undifferentiated stem cells found in the throughout the adult body even after embryonic development. Adult stem cells have site-specific differentiation ability that differentiates the cells themselves depending on the characteristics of surrounding tissue. Adult stem cells may originate from various adult cells such as bone marrow, blood, brain, skin, fat, skeletal muscle, umbilical cord, and umbilical cord blood. Specifically, examples of adult stem cells include, but are not limited to, mesenchymal stem cells, skeletal muscle stem cells, hematopoietic stem cells, neural stem cells, hepatic stem cells, adipose-derived stem cells, adipose-derived progenitor cells, and vascular endothelial progenitor cells.

Induced pluripotent cells, also as known as iPSCs or reprogrammed stem cells, are a type of pluripotent stem cells such as embryonic stem cells, that can be generated by expressing 4 kinds of specific reprogram-inducing genes after introducing the genes to non-pluripotent adult somatic cells such as skin cells, or by putting reprogram-inducing proteins extracted from cells which 4 kinds of specific genes are introduced into somatic cells. Induced pluripotent cells can replace cells damaged by diseases such as Parkinson's disease or type I diabetes. Induced pluripotent stem cells are used in a stem cell treatment using induced pluripotent stem cells, and cell-based researches of disease models and development of new drugs by studying progression of various diseases by in vitro differentiating induced pluripotent cells generated from somatic cells of patients.

Progenitor cells are cells before getting a specific form and a function, and are able to differentiate into specific cell lines or specific types of tissues. Progenitor cells refer to cells with self-renewal but very limited differentiating potency. Endodermal precursor cells, mesodermal precursor cells and ectodermal precursor cells are all included in the progenitor cells.

Animal cells are functional and structural basic unit originating from animals including humans. The animal cells of the present invention may include any cells originating from animals including humans In the present invention, examples of animal cells may be, but are not limited to, epithelial cells, endothelial cells, muscle cells, germ cells, skin cells (e. g. fibroblasts, keratinocytes), immune cells or cancer cells. Specifically, it may be, but is not limited to, exemplified that CHO (Chinese hamster ovary) cells, NSO (mouse myeloma) cells, BHK (baby hamster kidney) cells, Sp2/0 (mouse myeloma) cells, human retinal cells, HUVEC cells, HMVEC cells, COS-1 cells, COS-7 cells, HeLa cells, HepG-2 cells, HL-60 cells, IM-9 cells, Jurkat cells, MCF-7 cells or T98G cells.

Cells capable of being cultured in medium of the present invention include primary cells. Primary cells are cells cultured on the culture dish directly after being separated from an organ or a tissue of an individual. Generally, most cells grow with adhering to a culture dish. The cells continuously grow and form monolayer on the bottom of the culture dish, and the cell growth stops when there's no space for the cell to adhere anymore, of which culturing of primary cells is called as a primary culture. In case of culturing primary cells, a primary cell culture medium has been mainly used, because desired cell growth effect cannot be obtained by using a basal medium. A culture medium currently used have had many limitations that researches and experiments are not progressed well, because of high cost burden of the primary cell culture medium being 10 times more expensive than basal medium due to import dependency. Therefore, serum-free culture using compositions of medium additives and a medium composition of the present invention may allow cheaper and more efficient culture of primary cells.

The culture methods considered for culturing various cells may be the culturing method known well for culturing each cell in the art Effects of the Invention The present invention provides medium additives that can culture and allow cells to proliferate in serum-free culture systems, and the serum-free culture of the cells using the medium additives, with being free of global supply shortage of animal serum and ethical issues associated with collection of serum from bovine fetus. The present invention can provide clearly defined cell culture environment so as to regulate the cell activity in consistent manner, unlike the serum whose components are not clearly defined, and safer cells by preventing fundamentally from the contamination of animal substances.

BRIEF DESCRIPTION OF THE DRAWINGS

FIG. 1 shows a map of a plasmid (pCMV-SC-CF-H-WT-PXDN) to express recombinant human PXDN.

FIG. 2a shows a structure of a wild type human PXDN (WT), a PXDN variant in which ECM motif of N-terminal is deleted (ΔN), and a PXDN variant in which peroxidase domain is deleted (ΔP). FIG. 2b shows a process of establishing cell lines expressing stably the wild type PXDN and the deletion mutants, adding the conditioned medium (CM) of the cells to the XDN-depleted cells, and measuring the cell growth, and the results thereof. FIG. 2c shows the result of measurement of the activity of peroxidase.

FIG. 3a shows the procedure of purification of recombinant PXDN from the conditioned medium (CM) of the cell line expressing wild type human PXDN (HEK293-H-WT-PXDN). FIG. 3b shows the SDS-PAGE analysis result of the CM, the SDS-PAGE result of the PXDN protein and the P-60 protein purified from the CM and the dot blot result after treating with PXDN antibodies to the purified PXDN protein and P-60 protein. FIG. 3c shows the SDS analysis result of the purified PXDN protein under non-reducing and reducing conditions. FIG. 3d shows the result of measurement of the peroxidase activity of the purified PXDN protein and P-60 protein.

FIG. 4a shows the result of measurement of the degree of cell proliferation when PXDN-depleted cells were treated with recombinant PXDN (rPXDN) protein and bFGF. FIG. 4b shows the result of measurement of the degree of cell survival when PXDN-depleted cells were treated with recombinant PXDN (rPXDN) without adding bFGF.

FIG. 5a is a drawing illustrating the process of treating the cells with bFGF only or bFGF and recombinant PXDN (rPXDN) after treating HUVECs with siRNAs targeting PXDN or Collagen IV (siPXDN, siCol IV), or control siRNAs (siCTL). FIGS. 5b and 5c show the result of immunofluorescence staining of PXDN, Col IV, FN, or LAM, after treating HUVECS with siRNAs targeting PXDN or Collagen IV or control siRNA (Scale bar: 20 µm). In addition, FIG. 5d shows the Western blot result that monomer and dimer of collagen IV NC1 domain are detected after treatment with each siRNA, and the Western blot result which shows a degree of phosphorylation of ERK1/2 and FAK stimulated by the growth factors after treatment with each siRNA. FIG. 5e represents the immunofluorescence staining result of HUVEC cells treated with bFGF only or bFGF and rPXDN after siPXDN treatment (Scale bar: 20 µm).

FIG. 6a shows the Western blot result detecting p-ERK1/2 and ERK1/2 levels of HUVECs treated with bFGF, purified rPXDN or P-60 protein. FIG. 6b shows the result of measurement of a degree of cell proliferations of HUVECs, HMVECs, BM-MSCs and T98G cells treated by bFGF, or rPXDN or P-60 protein together with bFGF. FIG. 6c shows the result of measurement of the degree of cell survival when HUVECs are treated with rPXDN or P-60 protein without adding growth factors. FIG. 6d shows the result of measurement of the degree of cell proliferation when HUVECs were treated rPXDN or P-60 protein at various concentrations together with bFGF. FIG. 6e shows the result of measurement of the degree of cell proliferation when HUVECs were treated with rPXDN or P-60 together with various growth factors (VEGF or EGF).

FIG. 7a represents that PXDN is expressed even in the iPS cells originated from the cord blood mononuclear cells, and FIG. 7b shows a representative image of iPS cells (left), and a graph of result of measurement of the degree of cell proliferation (right) when iPS cells were cultured in the rPXDN (100 nM)-added feeder free culture medium.

MODE FOR CARRYING OUT THE INVENTION

Hereinafter, the present invention will be described in detail by examples. However, the following examples are just for illustrating the present invention, and do not serve to limit the scope of the present invention.

EXAMPLE 1

Cell Culture and Reagents

Human umbilical vein endothelial cells (HUVECs) were isolated from umbilical cords of newborn babies according to a procedure described previously (Jaffe, Nachman et al. 1973). Human umbilical cord samples were collected by procedures approved by the Institutional Review Board at The Catholic University of Korea, College of Medicine (approval No. CUMC09U157). Human microvascular endothelial cells (HMVECs) and bone marrow mesenchymal/stem cells (BM-MSCs) were purchased from Lonza. T98G and HEK293 cells were purchased from ATCC. HUVECs were cultured in M199 medium supplemented with 20% fetal bovine serum (FBS, Gibco), 30 µg/ml endothelial cell growth supplements (ECGS, BD Biosciences), 90 µg/ml heparin, and 1% antibiotics. HMVECs were cultured in endothelial growth medium 2 (EGM2)-MV medium (Lonza). BM-MSCs were cultured in Dulbecco's Modified Eagle Medium (DMEM, Invitrogen) medium supplemented with 20% FBS and 1% antibiotics. Other cells were cultured in DMEM supplemented with 10% FBS and 1% antibiotics.

EXAMPLE 2

Construction of Plasmids Expressing Recombinant Human PXDN and Deletion-Mutant PXDN cDNA of the human PXDN was purchased from Open Biosystems (Cat No BC140295). The PXDN open reading frame sequence was amplified by PCR using a PCR primer set (forward primer: GCCGCCATGGCCAAGCGCT (SEQ ID NO: 1), reverse primer: GGAGGGCTTTTCCTCCGCC (SEQ ID NO: 2)) and inserted into the cloning site of pCMV-SC-CF vector (Stratagene), the mammalian expression vector, to construct human wild-type PXDN-expressing plasmid (pCMV-SC-CF-H-WT-PXDN). The deletion-mutants were produced by filling sticky ends using Klenow enzyme (Takara) and self-ligation after cutting the plasmid (pCMV-SC-CF-H-WT-PXDN) with the following restriction enzymes: Bgl II and Sal I (deletion of 201-2086 bp which is N-terminal ECM motifs, ΔN) or Sal I and BspE I (deletion of 2086-3317 bp which is peroxidase domain, ΔP). The sequence of insert DNA was confirmed by DNA sequencing.

EXAMPLE 3

Expression and Purification of Recombinant Human PXDN Protein (rPXDN)

PXDN expressing HEK293 cells were obtained by transfection of the HEK293 cells with the recombinant plasmid expressing human PXDN (pCMV-SC-CF-H-WT-PXDN) or recombinant plasmid expressing deletion variant PXDN respectively, and selection by treating with G418 (Sigma) 800 µg/ml for 2 weeks. rPXDN-expressing HEK293 cells were cultured confluently to 80-90%, and the medium was then changed to serum-free DMEM. After culturing further for 24 h, conditioned medium (CM) was collected by obtaining supernatant and centrifuging at 3,000 rpm. After concentration of the obtained CM using a 3 kDa molecular weight-cutoff ultrafiltration cell (Amicon, Millipore), buffer change by repeated dilution with 20 mM potassium phosphate buffer (pH 8.0) and re-concentration was performed.

The concentrated solution was loaded onto a Q exchange spin column (Thermo Scientific). After washing with 25 mM NaCl in 20 mM potassium phosphate buffer (pH 8.0), the rPXDN was eluted with 1 M NaCl in 20 mM potassium phosphate buffer (pH 8.0). After the salt concentration of the pooled eluent was adjusted, the solution was loaded onto a Sephacryl S-300 (GE Healthcare) and fractionized by 20 mM potassium phosphate buffer containing 150 mM NaCl (pH 7.2-7.5). Then, the purified protein was concentrated using a Centricon centrifugal filter device (cutoff: 100 kDa; Millipore). Endotoxin was removed from the sample for cell assays by extraction with Triton X-114 followed by treatment with SM-2 beads (Aida and Pabst, 1990). An aliquot was subjected to SDS-PAGE, followed by staining with Coomassie Blue.

EXAMPLE 4

Peroxidase Activity Assay

150 µL of CM or rPXDN solution was added to 96-well plates, and treated with 50 µL 3,3',5,5'-Tetramethylbenzidine (TMB) substrate solution (Sigma). After incubation for 30 min, the light absorbance was measured at 650 nm.

EXAMPLE 5

RNA Interference and Cell Transfection siRNAs targeting PXDN or Collagen IV and control siRNA (siCTL) were obtained from ST Pharm. Co. (Seoul, Korea). The siRNA sequences are as the follow: for PXDN knockdown; forward, GCAUCAAUGCUGGCAUCUUTT (SEQ ID NO: 3), reverse, AAGAUGCCAG-CAUUGAUGCTT (SEQ ID NO: 4), for Col IV knockdown; forward, CCUCAUCUGUGAUAUAGACGGAUAUTT (SEQ ID NO: 5), reverse, AUAUCCGUCUAUAUCACA-GAUGAGGTT (SEQ ID NO: 6), for siCTL; forward; GUUCAGCGUGUCCGGCGAGTT (SEQ ID NO: 7), reverse, CUCGCCGGACACGCUGAACTT (SEQ ID NO: 8). Cells were seeded at a density of 30 cells/mm$^2$ and cultured for 24 h and the cells were transfected with 50 nM siRNA using lipofectamine RNAiMAX (Invitrogen). After 4 h, the cells were washed with PBS and then incubated in fresh culture medium for 48 h.

EXAMPLE 6

Cell Proliferation Assay

Cells were cultured in 96-well plate for 24 h. After a change to suitable fresh medium, the cells were kept in culture for 48 h. After 4 h of reaction with added 20 µL MTS reagent (Promega), the light absorbance was read at 490 nm using an ELISA reader (Molecular Devices) to investigate the cell proliferation level. For complementation assay, PXDN deficient HUVECs that were obtained by siRNA transfection and culturing for 48 h were cultured with rPXDN at several concentrations or CM, in the presence or absence of 10 ng/ml bFGF for 48 h. For experimental groups in which siRNA untreated naïve cells were treated with rPXDN, the cells was cultured for 48 h in serum-free medium containing each recombinant protein and 10 ng/ml bFGF, EGF, or VEGF.

EXAMPLE 7

Immunofluorescence Analysis

Cells were washed with PBS, fixed with 100% methanol for 5 min and treated with 0.1% Triton X-100 for 3 min. Nonspecific protein binding sites was blocked with 5% BSA for 1 h. The cells were incubated with primary antibodies, washed 3 times with PBS, and incubated with secondary antibodies conjugated with Alexa 488 (Invitrogen) or Cy 3 (Millipore) for 2 h. The following primary antibodies/dilutions were used: PXDN (1:500), fibronectin (FN; clone IST-4, 1:100, Sigma), Col IV (clone CIV 22, 1:100, DAKO) and laminin (LAM; 1:100, Abcam). As a negative control, the primary antibody was replaced by buffer. 1 µg/ml DAPI (Sigma) was added to the slides to stain nucleus. Images were obtained with a confocal microscope (Zeiss LSM 510 Meta with LSM image examiner software). For complementation assay, PXDN-deficient HUVECs that ware obtained by siRNA transfection and culturing for 48 h, were cultured with rPXDN in the presence of 10 ng/ml bFGF for 48 h. Then, the cells were fixed and immunofluorescence staining was performed. Fluorescence images were analyzed with NIH Image J program.

EXAMPLE 8

Detection of NC1 Sulfilimine Crosslink

The level of NC1-domain sulfilimine crosslinking in Col IV was assessed according to a procedure described previously (Lazar, Peterfi et al. 2015). 72 h-cultured HUVECs after each siRNA transfection, were washed with 300 mM HEPES (pH 7.4). Cell lysates were obtained by scraping up in hypotonic lysis buffer (10 mM CaCl2, 50 mM Hepes, pH7.4) containing 0.1 mM benzamidine hydrochloride (Sigma), 1 mM PMSF (Gibco), and 1 mM N-ethylmaleimide (Sigma). After reaction of the cell lysate with 0.5 mg/ml collagenase (Gibco) at 37° C. for 24 h, Western blot was performed. Monomer and dimer of collagen IV NC1 domains were detected with Col IV a2 antibody (Chondrex Inc) and horseradish peroxidase (HRP)-conjugated secondary antibody

EXAMPLE 9

Western Blot

Cells were lysed in lysis buffer [50 mM Tris (pH 8.0), 150 mM NaCl, 1% Triton X-100, 1% sodium deoxycholate, 0.1% SDS, 1 mM Na3VO4, 50 mM NaF, 1 mM EDTA, 1 mM EGTA, 2 mM PMSF, 1 µg/ml pepstatin, and protein inhibitor mix (Roche)], and the supernatant was obtained by centrifugation of the cell lysate at 14,000 rpm for 30 min, and the separated proteins were transferred to nitrocellulose membrane after the supernatant was subjected to 8% SDS-PAGE. To block nonspecific protein binding, the membrane was treated with 5% skim milk for 1 h, and the immune-response of protein bands were detected using ECL kit (Amersham) after treating the primary antibody and the secondary antibody conjugated with HRP in serial. The following antibodies were used as the primary antibodies: Flag-tag (Abcam), β-actin (Sigma), p-ERK1/2 (Cell Signaling), ERK1/2 (Cell Signaling), p-FAK (R&D Systems) and FAK (Millipore).

EXAMPLE 10

Cell Proliferation Assay of Induced Pluripotent Stem Cells 10-1: iPS Cell Culture iPS cells originated from cord blood mononuclear cells (CMC-7) were obtained from Professor Ji Hyeon Ju of Catholic university of Korea (Stem Cells Int. 2016; 2016: 1329459). The CMC-7 cells were seeded to a plate coated with vitronectin (0.5 ug/ml, Gibco), and cultured in the TeSR-E8 (Stemcell) medium. The medium were changed every 24 hours.

10-2: iPS Cell Proliferation Assay 96-well plate was coated with 0.5 ug/ml vitronectin 50 ul in 4° C. Cultured CMC-7 iPS cells were treated with 0.05% trypsin-EDTA and added with 5 ml TeSR-E8 medium, and centrifuged (1300 rpm, 5 min). After removing supernatant, the cells were suspended in TeSR-E8 medium with 10 uM ROCK inhibitor (Y27632, Sigma), and 1500 cells were seeded in each well of 96-well plate coated with vitronectin, and cultured for 24 h. After that, the medium was changed with TeSR-E8 medium with 100 nM rPXDN, followed by cultivation for 120 h. While culturing, medium was changed to rPXDN-added medium every 24 h. After that, 20 μl MTS reagent (Promega) were added and incubated for 3 h, and the light absorbance was read at 490 nm using an ELISA reader (Molecular Devices) to investigate the cell proliferation level to compare to controls.

EXAMPLE 11

Statistical Analysis

Data were presented as means±SEM of representative experiments. One-way ANOVAs with Tukey tests were used to compare results between the control and the samples using GraphPad Prism 5 (GraphPad Software). * $p<0.05$,  $p<0.01$, * $p<0.001$.

<<Experimental Results>>

1. Establishment of a Cell Line Expressing PXDN and Investigation of CM Activity: Comparative Analysis with Deletion-Mutant PXDN Human PXDN cDNA (aa 1-1479) was inserted into a mammalian expression plasmid vector (pCMV SC-CF) between the cytomegalovirus promoter and Flag-tag to produce a recombinant plasmid carrying PXDN sequence (pCMV-SC-CF-H-WT-PXDN; FIG. 1). Unlike other peroxidases, PXDN contains ECM motives comprising immunoglobulin C2 (IgC2)-type domain, leucine-rich repeats (LRR), and von Willebrand factor type C (vWC). Therefore, it was investigated whether PXDN is secreted out of the cell and act extracellularly as a component of CM, and whether the ECM motif and peroxidase domain are essential for PXDN function. A stable cell line expressing recombinant human PXDN (rPXDN) was established by transfection of HEK293 cells with recombinant plasmid (pCMV-SC-CF-H-WT-PXDN), and the cell line was named HEK293-H-WT-PXDN. In addition, stable cell lines named HEK293-H-ΔN-PXDN and HEK293-H-ΔP-PXDN respectively were constructed by transfecting HEK293 cells with plasmids expressing mutant PXDN with deficient N-terminal ECM motifs (ΔN) or peroxidase domain (ΔP) (FIG. 2a).

The cell lines are cultured in serum-free medium (EBM), and the conditioned medium (CM) was obtained by collecting supernatant. Cell proliferation was measured after adding CM to PXDN-depleted cells caused by PXDN siRNA knockdown and culturing for 48 h together with 10 ng/ml bFGF (FIG. 2b). It was observed that the cell proliferation was recovered enough when PXDN-depleted cells were treated with CM of HEK293-H-WT-PXDN expressing full-length PXDN, however, the cell proliferation could not be recovered at all in CM of HEK293-H-ΔN-PXDN or HEK293-H-ΔP-PXDN, like in CM obtained from cells in which empty vector is introduced (FIG. 2b).

In addition, there was no peroxidase activity observed in HEK293-H-ΔP-PXDN CM and empty vector CM, and the similar level of peroxidase activity was observed in HEK293-H-ΔN-PXDN and HEK293-H-WT-PXDN CM (FIG. 2c). The results indicate that both ECM motif and peroxidase domain are essential for PXDN function, suggesting that CM of PXDN expressing cell line can be used to promote cell proliferation.

2. Purification of rPXDN Protein

After obtaining CM by culturing a HEK293-H-WT-PXDN cell line, rPXDN protein were purified from CM, as described in examples, by sequential chromatography using anion exchange Q-spin column and Sephacryl S-300 size exclusion chromatography (FIG. 3a). Endotoxin from the sample was removed by extraction with Triton X-114, followed by treatment with SM-2 beads to remove the Triton X-114. The size of rPXDN was about 170 kDa when the CM and purified proteins were electrophoresed in a 6% SDS-PAGE gel under reducing condition (FIG. 3b). Unknown protein P-60 (about 60 kDa) that existed at the high level in the CM was also purified as a negative control protein.

Dot blot analysis was performed by PXDN antibody and it was shown that P-60 did not react with the antibody and only rPXDN reacted. Since the size of rPXDN was about 500 kDa in SDS-PAGE analysis under non-reducing condition, it was assumed that rPXDN exists as trimer form in CM (FIG. 3c). The concentration of rPXDN used in the experiment was determined at the basis of monomer. The peroxidase activity of purified rPXDN was increased in a dose dependent manner when the activity of purified rPXDN was measured by TMB oxidation methods (FIG. 3d). Therefore, it was confirmed that purified rPXDN forms trimers and has intact peroxidase activity.

3. rPXDN Compensates Proliferation and Survival of PXDN-Depleted HUVECs.

To investigate whether exogenous PXDN protein can compensate for function of PXDN knockdown cells, PXDN-deficient cells constructed by siRNA knockdown were cultured for 48 h after adding purified rPXDN (FIG. 4a). In the absence of the rPXDN, the proliferation of the PXDN-depleted cells caused by the siRNA transfection was markedly decreased compared with that of the siCTL-transfected cells (FIG. 4a). On the other hand, when PXDN-depleted cells were treated with rPXDN, it was shown that the proliferation of the cells was recovered upon addition of rPXDN in a dose-dependent manner The results suggest that PXDN functions extracellularly. Moreover, in the absence of bFGF, rPXDN treatment prevented cell death of the PXDN-depleted cells in a dose-dependent manner (FIG. 4b). These results suggest that purified rPXDN can fully compensate proliferation and survival of PXDN-depleted HUVECs.

4. rPXDN Restores the Assembly of Col IV, FN, and LAM into Dense Fibrillar Networks in PXDN-Depleted Cells The present inventors determined whether PXDN is required for the assembly of fibrillar networks in the pericellular ECM components of cells (FIG. 5a). It was observed that the assembly of Col IV was reduced significantly in PXDN-depleted cells and the ratio of NC1 dimer in Col IV formed by crosslinked sulfilimine bond also decreased (FIG. 5b to FIG. 5d). In addition, PXDN knockdown also drastically inhibited fibrillar network assembly of fibronectin (FN) and moderately inhibited laminin (LAM) assembly. Col IV knockdown cells had an inhibition of the fibrillar network assembly of FN and LAM similar to PXDN knockdown cells. PXDN depletion also resulted in decreased bFGF-stimulated or VEGF-stimulated phosphorylation of FAK and ERK1/2 probably due to defect of ECM assembly. The present inventors also investigated whether rPXDN could complement deficient ECM assembly of PXDN-depleted cells. As shown in FIG. 5e, rPXDN could restore the poor fibrillar network assembly of Col IV, FN, and LAM shown in PXDN-depleted cells. These data suggest that rPXDN could be used for ECM assembly or deposit of cells, in order for cells to undergo full ECM-mediated signaling for cellular function.

5. Promoting Cell Proliferation by rPXDN Treatment Without Direct Activation of ERK1/2 in Serum-Free Medium The present inventors tested whether purified rPXDN promotes cell proliferation in serum-free medium using naive cells. As shown in FIGS. 6a and 6b, direct activation of ERK1/2 did not occur in HUVECs when HUVECs were treated with purified rPXDN (100 nM), however it was found that cell proliferation of HUVECs was promoted by rPXDN treatment in the presence of bFGF. The growth of other primary cells (HMVECs, BM-MSC) as well as established cancer cell line (brain tumor cell line T98G) was also promoted by addition of purified rPXDN. Whereas protein P-60 purified from the CM did not show such effect.

Next, the present inventors investigated the effect to the cell survival and growth of HUVECs in absence of a growth factor by adding rPXDN in various concentrations followed by 48 h culture, and found that the cell survival was increased in rPXDN dose-dependent manner (FIG. 6c). In presence of bFGF, after 48 h culture with rPXDN, the cell proliferation of HUVEC was promoted in dose-dependent manner (FIG. 6d).

To determine whether the cell proliferation promoting effect is specific to bFGF or regardless of growth factor types, HUVECs were cultured with rPXDN in the presence of VEGF or EGF. P60 protein did not show cell proliferation promoting effect, but rPXDN showed significant cell proliferation promoting effect (FIG. 6e). Therefore, these results indicate that rPXDN can be used as adjuvants capable of promoting growth and survival in defined culture medium for culture of various cells such as stem cells and progenitor cells.

6. Promotion of iPS Cell Proliferation in Feeder Free Medium by rPXDN Treatment

To investigate whether iPS cells originated from cord blood mononuclear cells express PXDN, Western blot was carried out and it was found that CMC-7 cells which are iPS cells also expressed PXDN like HUVECs (FIG. 7a). The present inventors determined whether purified rPXDN promotes iPS cell proliferation in serum-free medium. As shown in FIG. 7b, the cell proliferation was promoted upon addition of purified rPXDN. Therefore, the result suggests that rPXDN can be used for feeder free cell culture of iPS cells.

The invention claimed is:

1. A method for promoting proliferation of cells in serum-free culture comprising a step of culturing cells in a medium for serum-free culture, wherein the medium comprises a medium additive composition comprising a recombinant vector comprising a peroxidasin gene, a cell transformed by the recombinant vector, or a purified peroxidasin.

2. The method of claim 1, wherein the medium additive composition further comprises a growth factor.

3. The method of claim 2, wherein the growth factor is at least one selected from the group consisting of fibroblast growth factor (FGF), vascular endothelial growth factor (VEGF), epidermal growth factor (EGF), connective tissue growth factor (CTGF), insulin-like growth factor (IGF), transforming growth factor (TGF), nerve growth factor (NGF), hepatocyte growth factor (HGF), platelet-derived growth factor (PDGF), bone-derived growth factor (BDGF), stem cell factor, leukemia inhibitory factor (LIF), brain-derived neurotrophic factor (BDNF), Glial-derived neurotrophic factor (GDNF), Activin A, Noggin, bone morphogenetic protein 2 (BMP2), bone morphogenetic protein 4 (BMP4), Angiopoietin-1, SHH (sonic hedgehog), Wnt, FLT-3 ligand (FMS-related tyrosine kinase 3 ligand) and colony stimulation factor (CSF).

4. The method of claim 1, wherein the growth factor is basic fibroblast growth factor (bFGF).

5. The method of claim 1, wherein the cell is cells are stem cells, progenitor cells, or animal cells.

6. The method of claim 5, wherein the stem cells are embryonic stem cells, adult stem cells, or induced pluripotent stem cells.

7. The method of claim 1, wherein the cell is cells are primary cells.

8. The method of claim 1, wherein the method is used for survival and proliferation of cells.

* * * * *

```
                        SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: forward primer

<400> SEQUENCE: 1
gccgccatgg ccaagcgct                                                   19

<210> SEQ ID NO 2
<211> LENGTH: 19
<212> TYPE: DNA
<213> ORGANISM: Artificial Sequence
<220> FEATURE:
<223> OTHER INFORMATION: reverse primer

<400> SEQUENCE: 2
ggagggcttt tcctccgcc                                                   19

<210> SEQ ID NO 3
<211> LENGTH: 21
<212> TYPE: DNA
<213> ORGANISM: Artificial Sequence
<220> FEATURE:
<223> OTHER INFORMATION: PXDN siRNA

<400> SEQUENCE: 3
gcaucaaugc uggcaucuut t                                                21

<210> SEQ ID NO 4
```

```
<211> LENGTH: 21
<212> TYPE: DNA
<213> ORGANISM: Artificial Sequence
<220> FEATURE:
<223> OTHER INFORMATION: PXDN siRNA

<400> SEQUENCE: 4
aagaugccag cauugaugct t                                              21

<210> SEQ ID NO 5
<211> LENGTH: 27
<212> TYPE: DNA
<213> ORGANISM: Artificial Sequence
<220> FEATURE:
<223> OTHER INFORMATION: Col IV siRNA

<400> SEQUENCE: 5
ccucaucugu gauauagacg gauautt                                        27

<210> SEQ ID NO 6
<211> LENGTH: 27
<212> TYPE: DNA
<213> ORGANISM: Artificial Sequence
<220> FEATURE:
<223> OTHER INFORMATION: Col IV siRNA

<400> SEQUENCE: 6
auauccgucu auaucacaga ugaggtt                                        27

<210> SEQ ID NO 7
<211> LENGTH: 21
<212> TYPE: DNA
<213> ORGANISM: Artificial Sequence
<220> FEATURE:
<223> OTHER INFORMATION: control siRNA

<400> SEQUENCE: 7
guucagcgug uccggcgagt t                                              21

<210> SEQ ID NO 8
<211> LENGTH: 21
<212> TYPE: DNA
<213> ORGANISM: Artificial Sequence
<220> FEATURE:
<223> OTHER INFORMATION: control siRNA

<400> SEQUENCE: 8
cucgccggac acgcugaact t                                              21
```